(12) United States Patent
Kurusu

(10) Patent No.: US 6,338,346 B1
(45) Date of Patent: Jan. 15, 2002

(54) ARTICLE WORN ON THE BODY

(76) Inventor: Masao Kurusu, Kita-ku (JP)

( * ) Notice: Subject to any disclaimer, the term of this patent is extended or adjusted under 35 U.S.C. 154(b) by 0 days.

(21) Appl. No.: 09/526,057

(22) Filed: Mar. 15, 2000

(30) Foreign Application Priority Data

Mar. 16, 1999 (JP) .......................................... 11-070553

(51) Int. Cl.⁷ .......................... A61B 19/00; A44C 13/00

(52) U.S. Cl. ........................................ 128/897; 63/1.11

(58) Field of Search ................................ 604/289, 304; 600/9, 8, 7, 15; 63/1.11, 3; 607/111; 128/897

(56) References Cited

FOREIGN PATENT DOCUMENTS

DE                 3830043 A1  *  3/1990

* cited by examiner

Primary Examiner—Eric F. Winakur
Assistant Examiner—Nikita R Veniaminov
(74) Attorney, Agent, or Firm—Sughrue Mion, PLLC

(57) ABSTRACT

Several kinds of metal members 6, 7 different in ionization trend are arranged to constitute an article worn on the body 1, and implementation of the different kind metal treatment can be made highly effectively and without a sense of incongruity even in the working place where one wears a suit, working clothes or the like and has to move the body. Preferably, the several kinds of metal members different in ionization trend are arranged in order of the magnitude of the ionization trend.

8 Claims, 5 Drawing Sheets

ARTICLE WORN ON THE BODY

BACKGROUND OF THE INVENTION

1. Field of the Invention

The present invention relates to an article worn on the body to be used wearing it on the body in order to improve a disease, a pain in the parts of the body, stiffness, a poor physical condition, and so on.

2. Description of the Prior Art

It is known that a fine current called a bioelectric current is always flowing in the human body such as to flow in a nerve cell when the brain functions, and in a myocardial cell when the heart contracts, and the bioelectric current controls various functions of the body. Further, it has been understood that when the bioelectric current is stagnated or disturbed in its flow under the influence of fatigue matter accumulated in muscles, static electricity generated in a sweater, a blanket or the like, an electromagnetic wave generated from a television set, a personal computer or the like, various functions of the body are lost in balance to show symptoms such as a disease, a pain in the parts of the body, stiffness, a poor physical condition, and so on.

Recently, therefore, an attempt has been made to employ various treatments for improving a disease, a pain in the parts of the body, stiffness, a poor physical condition, and so on by adjusting the flow of the bioelectric current, and among them, a different kind metal treatment is known whose effect is actually proved. According to the different kind metal treatment, metals different in ionization trend, for example, such as aluminum of a 1-Yen coin, zinc and copper of a 5-Yen coin, and tin and copper of a 10-Yen coin, are applied sequentially to the affected part showing symptoms or the right spot corresponding thereto, and the flow of the bioelectric current is adjusted by utilizing a potential difference generated due to a difference between the ionization trends.

However, in the scene for actually implementing the above-described different kind metal treatment, metals different in ionization trend, are applied sequentially to the affected part showing symptoms or the right spot corresponding thereto. Therefore, this treatment can be implemented in a hospital, a home or the like where one can wear relatively rough clothes and lie quietly, but in a working place where one wears a suit, working clothes or the like and has to move the body, metals cannot be applied positively, and being poor-looking. Thus, in the real state, the different kind metal treatment could not be implemented.

SUMMARY OF THE INVENTION

The present invention has been accomplished in the light of problems as noted above with respect to prior art. It is an object of the invention to enable implementation of the different kind metal treatment highly effectively and without a sense of incongruity even in the working place where one wears a suit, working clothes or the like and has to move the body.

For achieving the aforesaid object, according to the present invention, several kinds of metals different in ionization trend are arranged as component members to constitute an article worn on the body.

Preferably, the above-described several kinds of metals different in ionization trend are arranged in order of the magnitude off the ionization trend.

The present invention can be applied to accessories such as an earring, a necklace, a pendant, a ring, a bracelet, an armlet, and an anklet.

DESCRIPTION OF THE PREFERRED EMBODIMENTS

The preferred embodiments of the present invention will be described hereinafter with reference to the drawings.

According to the present invention, several kinds of metals different in ionization trend necessary for implementing the different kind metal treatment are used to constitute accessories such as an earring, a necklace, a pendant, a ring, a bracelet, an armlet, and an anklet, and an article worn on the body such as under-clothes such as an undershirt, briefs, a brassiere, and panties.

Figure 1:
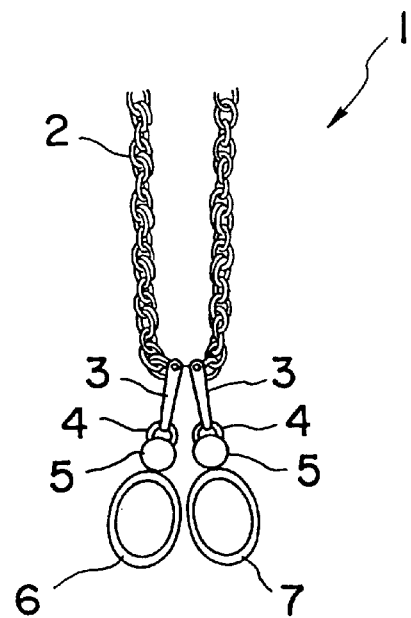
FIG. 1 is a front view showing an embodiment where the present invention is applied to a pendant.

FIG. 1 shows an embodiment where the present invention is applied to a pendant. A pendant 1 is constructed such that a chain 2 is caught with two hooks 3, 3, and metal members 6, 7 that imitate gems are connected to the hooks 3, 3 through links 4, 4 and side stones 5, 5.

The metal members 6, 7 are formed of different kind of stocks, employing metals different in ionization trend. Particularly, since a potential difference generated from a difference between the ionization trends is utilized, preferably, metals which relatively have a difference between the ionization trends are selected.

Metals are listed below in order of those having the great ionization trend:

$$K>Ca>Na>Mg>Al>Zn>Fe>Ni>Sn>Pb>(H)>Cu>Hg>Ag>Pt>Au$$

Thus, for example, aluminum (Al) can be employed as a stock for one of the metal members 6, 7, and copper (Cu) as a stock for the other.

Figure 2:
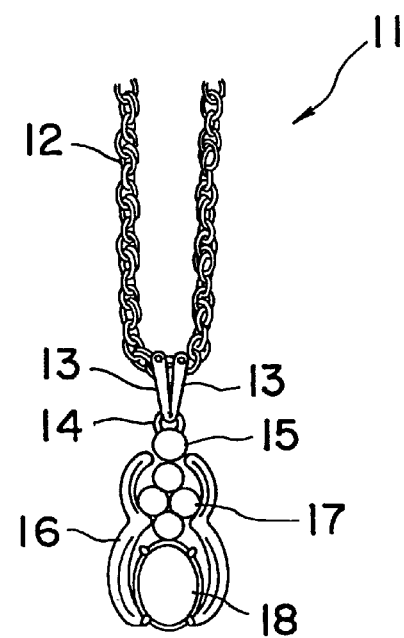
FIG. 2 is a front view showing a further embodiment where the present invention is applied to a pendant.

FIG. 2 shows a further embodiment where the present invention is applied to a pendant. A pendant 11 is constructed such that a chain 12 is caught with hooks 13, and a trim 16 is secured thereto through a link 14 and a side stone 15. a metal member 17 that imitates a side stone is connected to a side stone 15 so as to be held by the trim 16, and a metal member 18 that imitates a gem is connected thereto.

Similarly to the above, stocks for the metal members 17, 18 are different in kind, and metals which different in ionization trends are employed. For example, aluminum (Al) can be employed as a stock for one of the metal members 17, 18, and copper (Cu) as a stock for the other.

In case of applying to the pendant, the metal members 6, 7 different in ionization trend may be arranged closely, as in the pendant 1 shown in FIG. 1, or the metal members 17, 18 different in ionization trend may be connected and arranged, as in the pendant 11 shown in FIG. 2.

Alternatively, two kinds of metal members different in ionization trend can be adhered and integrated, though the therapeutic effect somewhat lessens.

If the neck is caught with the chain 2 (12) of the pendant 1 (11), and the metal members 6, 7 (17, 18) are positioned at the breast, a fine current flows between the metal members 6 and 7, or between the metal members 17 and 18 passing through the breast due to a potential difference between the ionization trends between the metal members 6 and 7, or between the metal members 17 and 18 to thereby enable adjustment of the flow of a bioelectric current whereby an ailment of the breast, a pain, a poor physical condition and so on can be improved.

Because of the form of the pendants 1, 11, even in a working place where one has to wear a suit, working clothes or the like and to move the body, the neck is merely caught with the pendants 1, 11, and the different kind metal treatment can be implemented highly effectively and without a sense of incongruity.

Figure 3:
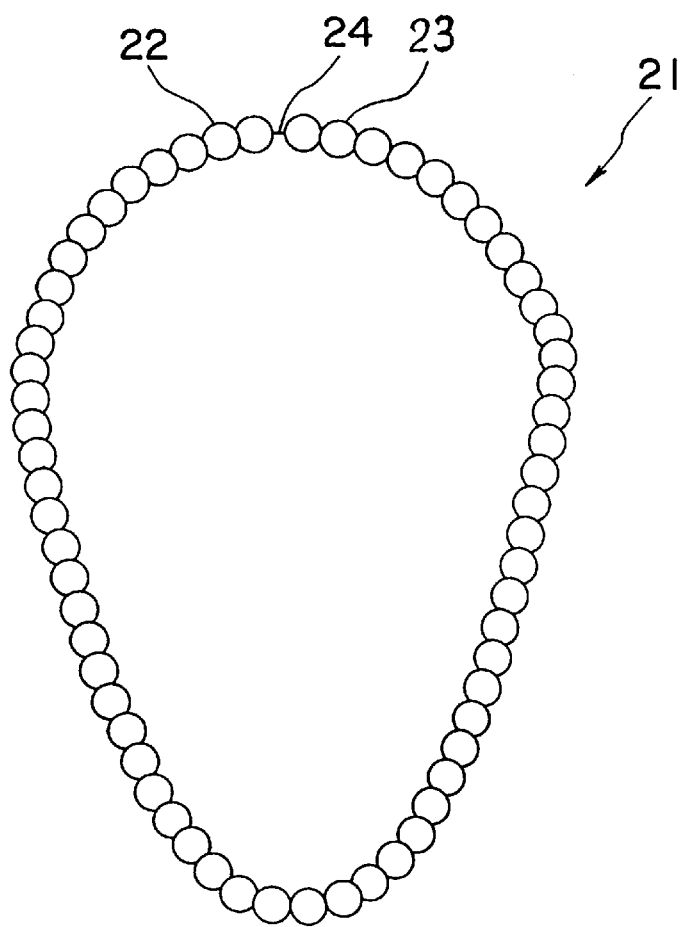
FIG. 3 is a front view showing an embodiment where the present invention is applied to a necklace.

FIG. 3 shows an embodiment where the present invention is applied to a necklace. A necklace 21 is constructed such that a string or a wire 24 is inserted through metal members 22 and 23 that imitate a pearl or a gem to connect them.

The left portion comprises the metal members 22, and the right portion comprises the metal members 23. Similarly to the above, stocks for the metal members 22, 23 are different in kind, and metals which different in ionization trends, for example, aluminum (Al) and copper (Cu) are employed.

Instead that the left portion comprises the metal members 22, and the right portion comprises the metal members 23 the necklace 21 is suitably divided in a longitudinal direction, the divided portions are constituted by different metal members, and the different metal members can be connected alternately.

If the neck is caught with the necklace 21, a fine current flows between the metal members 22 and 23 passing through the neck, the shoulders, and the breast due to a potential difference between the ionization trends between the metal members 22 and 23 to thereby enable adjustment of the flow of a bioelectric current whereby an ailment of the neck, the shoulders, and the breast, a pain, stiffness, a poor physical condition and so on can be improved.

Figure 4:
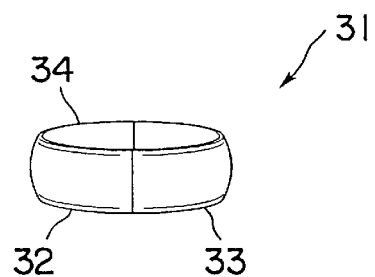
FIG. 4 is a perspective view showing an embodiment where the present invention is applied to a ring.

FIG. 4 is a perspective view shows an embodiment where the present invention is applied to a ring 31. The ring 31 is constructed such that semi-annular metal members 32, 33 are connected peripherally to constitute a shank 34.

Similarly to the above, stocks for the metal members 32, 33 are different in kind, and metals which different in ionization trends, for example, aluminum (Al) and copper (Cu) are employed.

Instead that the semi-annular metal members 32, 33 are connected peripherally, annular different metal members can be connected widthwise. Further, annular different metal members may be adhered thickness-wise and integrated, though the therapeutic effect somewhat lessens.

If the ring 31 is put on the finger, a fine current flows between the metal members 32 and 33 passing through the finger due to a potential difference between the ionization trends between the metal members 32 and 33 to thereby enable adjustment of the flow of a bioelectric current whereby an ailment of the finger, a pain and so on can be improved.

Figure 5:
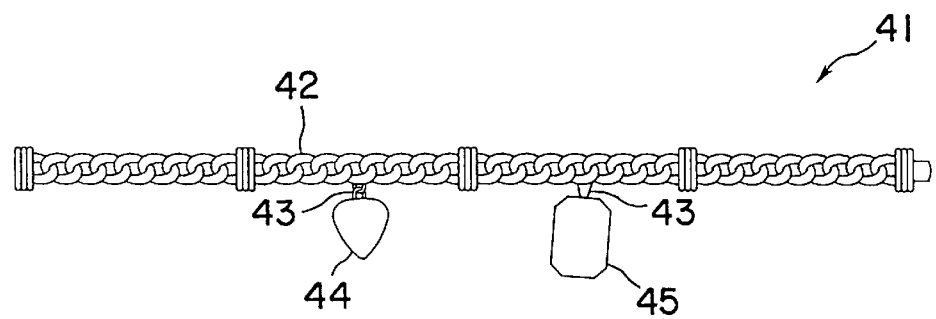
FIG. 5 is a front view showing an embodiment where the present invention is applied to a bracelet.

FIG. 5 is a front view shows an embodiment where the present invention is applied to a bracelet 41. The bracelet 41 is constructed such that metal members 44, 45 are connected as charms to a chain 42 through links 43, 43.

Similarly to the above, stocks for the metal members 44, 45 are different in kind, and metals which different in ionization trends, for example, aluminum (Al) and copper (Cu) are employed.

Instead that the metal members 44, 45 are connected as charms, the chain 42 is suitably divided in a longitudinal direction, the divided portions are constituted by different metal members, and the different metal members may be connected alternately.

If the bracelet 41 is put on the wrist, a fine current flows between the metal members 44 and 45 passing through the wrist due to a potential difference between the ionization trends between the metal members 44 and 45 to thereby enable adjustment of the flow of a bioelectric current whereby an ailment of the wrist, a pain, stiffness, a poor physical condition and so on can be improved.

Figure 6:
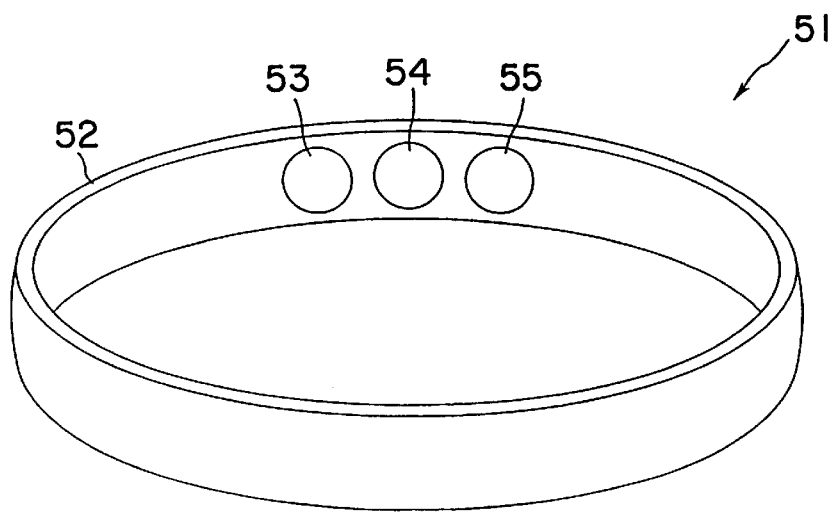
FIG. 6 is a front view showing an embodiment where the present invention is applied to an anklet.

FIG. 6 shows an embodiment where the present invention is applied to an anklet 51. The anklet 51 is constructed such that metal members 53, 54, 55 in the form of a sheet are arranged and adhered close to the inner peripheral surface of a band 52 formed of leather, rubber or the like.

Similarly to the above, stocks for the metal members 53, 54, 55 are different in kind, and metals which different in ionization trends, for example, aluminum (Al), nickel (Ni) and copper (Cu) are employed.

Instead that the metal members 53, 54, 55 are adhered close to the inner peripheral surface of the band 52, the band 52 is suitably divided in a longitudinal direction, the divided portions are constituted by different metal members, and the different metal members may be connected alternately.

If the anklet 51 is put on the ankle, a fine current flows between the metal members 53, 54, 55 passing through the wrist due to a potential difference between the ionization trends between the metal members 53, 54, 55 to thereby enable adjustment of the flow of a bioelectric current whereby an ailment of the ankle, a pain, stiffness, a poor physical condition and so on can be improved.

Figure 7:
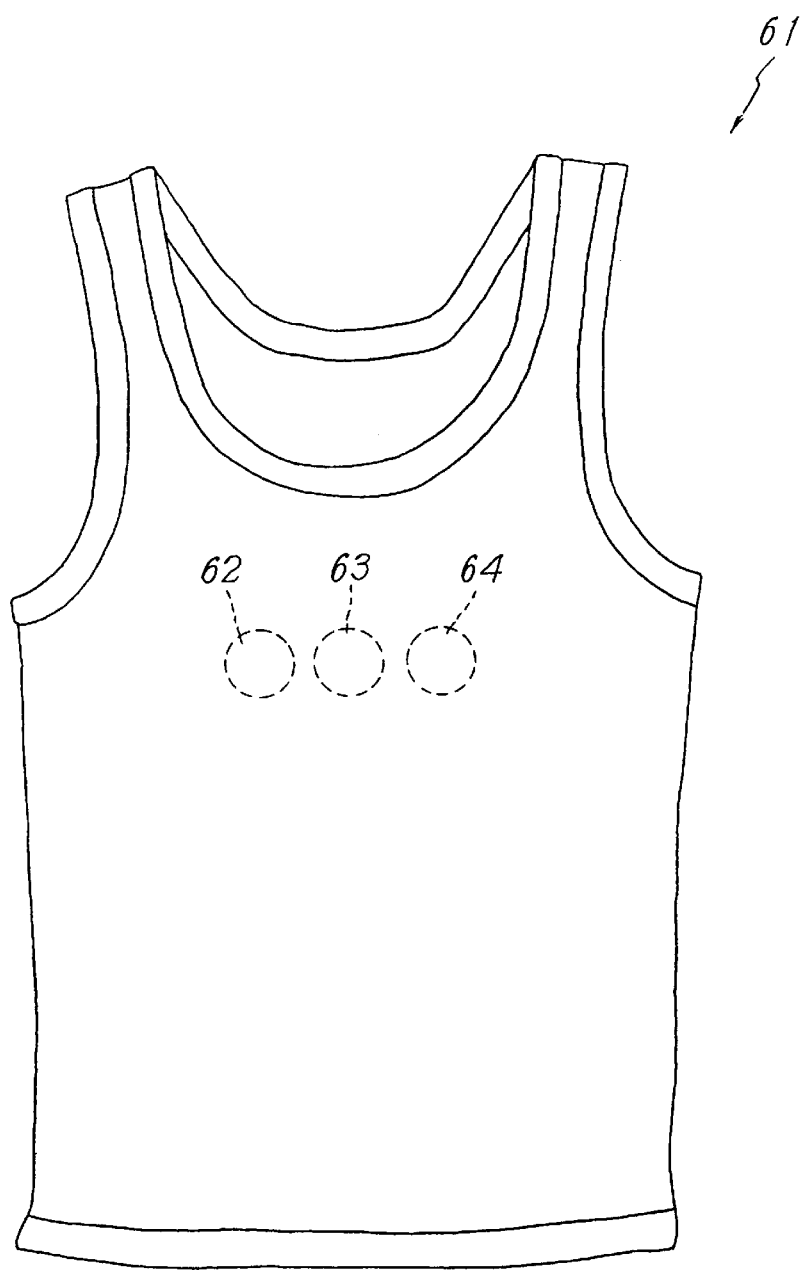
FIG. 7 is a front view showing an embodiment where the present invention is applied to an undershirt.

FIG. 7 shows an embodiment where the present invention is applied to an undershirt 61. The undershirt 61 is constructed such that metal members 62, 63, 64 in the form of a sheet are arranged close to the inner surface of the back and adhered.

Similarly to the above, stocks for the metal members 62, 63, 64 are different in kind, and metals which different in ionization trends, for example, aluminum (Al), nickel (Ni) and copper (Cu) are employed.

If the undershirt 61 is worn, a fine current flows between the metal members 62, 63, 64 passing through the back due to a potential difference between the ionization trends between the metal members 62, 63, 64 to thereby enable adjustment of the flow of a bioelectric current whereby an ailment of the back, a pain, stiffness, a poor physical condition and so on can be improved.

Instead that the metal members 62, 63, 64 in the form of a sheet are adhered close to the inner peripheral surface of the back, they may be adhered to the inner surface of the shoulder or the inner surface of the breast whereby an ailment of the shoulder and the breast, a pain, stiffness, a poor physical condition and so on can be improved.

Figure 8:
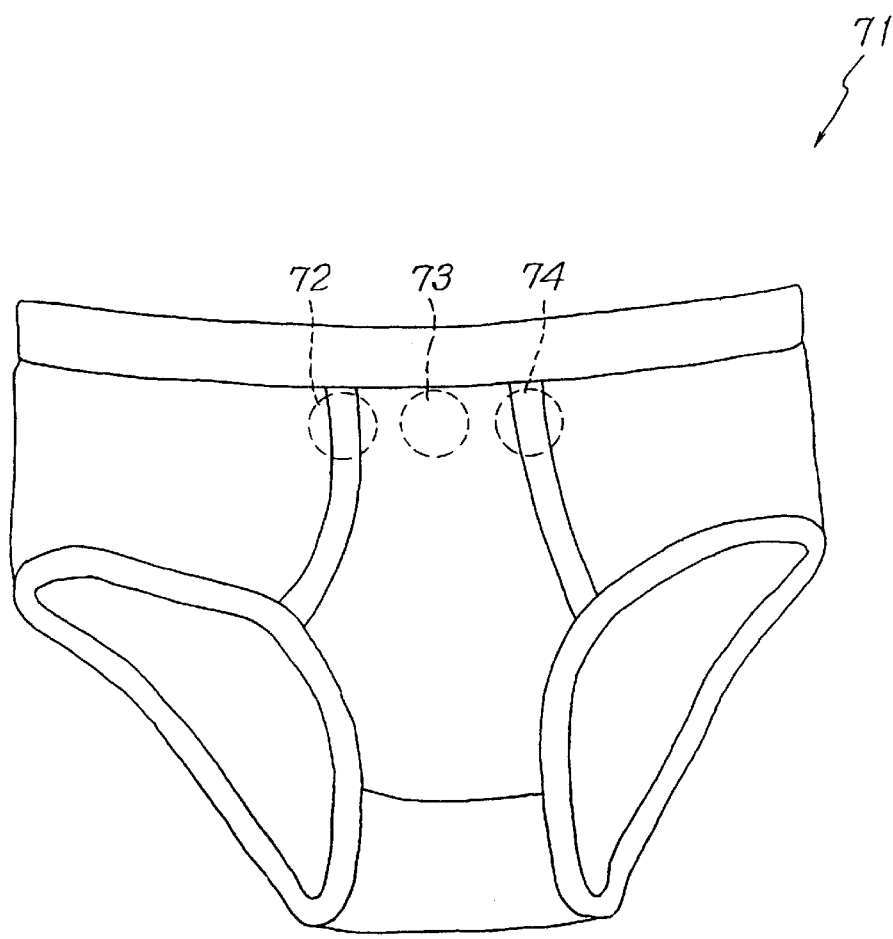
FIG. 8 is a perspective view showing an embodiment where the present invention is applied to briefs.

FIG. 8 shows an embodiment where the present invention is applied to briefs 71. The briefs 71 is constructed such that metal members 72, 73, 74 in the form of a sheet are arranged close to the inner surface of the waist and adhered.

Similarly to the above, stocks for the metal members 72, 73, 74 are different in kind, and metals which different in ionization trends, for example, aluminum (Al), nickel (Ni) and copper (Cu) are employed.

If the briefs 71 is worn, a fine current flows between the metal members 72, 73, 74 passing through the waist due to a potential difference between the ionization trends between the metal members 72, 73, 74 to thereby enable adjustment of the flow of a bioelectric current whereby an ailment of the waist, a pain, stiffness, a poor physical condition and so on can be improved.

Instead that the metal members 72, 73, 74 in the form of a sheet are adhered to the inner peripheral surface of the waist, they may be adhered to the inner surface of the belly whereby an ailment of the belly, a pain, stiffness, a poor physical condition and so on can be improved.

It is to be noted that the metal members different in ionization trend used to constitute the article worn on the body are not limited to 2 or 3 kinds, but suitable kinds of metal members can be used.

However, where more than three kinds of metal members are used, it is necessary to take the arranging order and the connecting order of the metal members into consideration, in consideration of the direction of a fine current. More specifically, it is preferable to arrange and connect them in order of the magnitude of the ionization trend.

Since the article worn on the body according to the present invention remains the same as that of prior art in external appearance and function, it is easily detachable, and since that is not adhered to the skin directly, the skin is less poisoned therewith.

Particularly, in case of accessories, they are very easily detachable, and are adhered to and moved away from the skin. Therefore, the skin is not poisoned therewith. There is an effect that a flow of a fine current is turned ON and OFF, lessening stimulation to the body, which is more preferable.

Furthermore, since a fine current flows into the body when the article is worn, there is an effect that static electricity is not accumulated on the surface of the body. Particularly in the winter season or the like, local discharge caused by static electricity can be prevented.

What is claimed is:

1. An article worn on the body comprising:

a first metal member comprising a metal having a first ionization quality, a second metal member comprising a metal having a second ionization quality; and a third metal member comprising a metal having a third ionization quality, said first, second and third ionization qualities differing in ionization trend and said metals being arranged in order of the magnitude of the ionization trend.

2. The article worn on a body according to claim 1, wherein said first metal member, second metal member and third metal member are arranged in a line.

3. The article worn on the body according to claim 2, wherein the first metal member, the second metal member and the third metal member are spaced apart along said line.

4. The article worn on the body according to claim 3 further comprises a support medium to which said first, second and third members are affixed.

5. The article worn on the body according to claim 4, wherein said support medium is non-conductive.

6. The article worn on the body according to claim 5, wherein said support medium comprises an article of clothing.

7. The article worn on the body according to claim 5, wherein said support medium comprises a decorative article.

8. The article worn on the body according to claim 1, wherein the first metal member, the second metal member and the third metal member are separated but arranged closely adjacent to another member at a distance selected to adjust the generation and flow of a bio-electric current.

\* \* \* \* \*